United States Patent
Balentine et al.

(10) Patent No.: US 6,491,961 B1
(45) Date of Patent: Dec. 10, 2002

(54) COLD BREW TEA

(75) Inventors: Douglas Ashley Balentine, River Vale, NJ (US); Steven Alphonse Gobbo, Secaucus, NJ (US); Robert Steven Hang, Fairlawn, NJ (US); Xiaoqun Qi, Hackensack, NJ (US); Andrew David Parry, Sharnbrook (GB); Christopher William Goodsall, Sharnbrook (GB)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/498,081

(22) Filed: Feb. 4, 2000

Related U.S. Application Data (60) Provisional application No. 60/119,102, filed on Feb. 8, 1999.

(51) Int. Cl.[7] .................................................. A23F 3/10
(52) U.S. Cl. .......................................... 426/597; 426/49
(58) Field of Search .................................. 426/597, 435, 426/49

(56) References Cited

U.S. PATENT DOCUMENTS

| | | |
|---|---|---|
| 3,812,266 A | 5/1974 | Sanderson et al. |
| 4,051,264 A | 9/1977 | Sanderson et al. |
| 4,639,375 A | 1/1987 | Tsai |
| 5,919,500 A | 7/1999 | Lehmberg et al. |

FOREIGN PATENT DOCUMENTS

| | | |
|---|---|---|
| EP | 0 760 213 A1 | 3/1997 |
| EP | 0 910 956 A1 | 4/1999 |
| GB | 1 413 351 | 11/1975 |
| GB | 1 546 508 | 5/1979 |
| WO | WO 97/40699 | 11/1997 |

OTHER PUBLICATIONS

Robertson 1992 (*Tea Cultivation Consumption*, Wilson, K.C. and Clifford, M.N. Eds., Chapman Hill, London).
Search Report Under Section 17.
International Search Report (PCT/EP 00/00906).
Database Abstract JPO & Japlo. Publication 02009341, Published Dec. 1, 1990, Inventor: Yokichi.

*Primary Examiner*—Anthony J. Weier (57) ABSTRACT

A cold water infusible tea leaf product is described which brews in cold water to produce an iced tea beverage with the color and flavor of iced teas prepared by hot brewing methods. The product when brewed in water at about 15° C. for about 5 minutes at a water to tea ratio of 100 water to 1 tea has a cold water infusion Hunter L Value of about 25 to 45; a Hunter "a" value of about 24 to 34; a Hunter haze value of less than 40 and at least 0.15% soluble tea solids.

7 Claims, 3 Drawing Sheets

COLD BREW TEA

This application claims the benefit of U.S. Provisional Application No. 60/119,102, filed Feb. 8, 1999.

The present invention generally relates to a cold water infusible tea leaf, to processes for obtaining such leaf and to the improved cold water infusion products thereby obtained.

BACKGROUND

Black tea is traditionally produced from fresh green tea leaves (*Camellia sinensis*) by a process comprising four major steps: withering, rolling, fermentation and firing. Withering is a process whereby the freshly plucked green tea leaves are stored until the moisture content is reduced to about 55–72% of the leaf weight. The withered leaves are crushed by rolling or maceration in order to break down the leaf cell structure and bring enzymes and the substrate polyphenols into contact. During fermentation the simple flavonoids in green tea leaf are oxidized by endogenous tea enzymes to produce the polyphenols that impart a bright red color and the astringent flavor to black tea. Tea fermentation is truly an enzymatic process and is not the typical fermentation used in brewing of alcoholic beverages. Two enzymes, polyphenol oxidase and peroxidase catalyze the oxidation of simple catechins to the more complex polyphenols; namely theaflavins (TF) and thearubigens (TR).

Fermented teas are fired (dried) with hot, dry air reducing the moisture content of the leaves to less than 5%. Firing of teas arrests fermentation by inactivating enzymes and results in development of color and flavor from chemical oxidation and creates the final balance of tea aroma. Following drying, the leaves are then sorted and graded to yield a commercial black tea product. The process of tea manufacture is described in great detail by Robertson 1992 (Tea: *Cultivation to Consumption*. Wilson, K. C. and Clifford, M. N., Eds., Chapman Hall, London)

Tea beverage is prepared from the black tea leaf manufactured by the above process by infusing the tea leaves loose or in a tea bag in hot freshly boiled water for a few minutes. After removing the tea leaf, the beverage is then consumed hot or cold as iced tea.

It is well known that the majority of the tea consumed in the U.S. is iced tea prepared by cooling down tea beverage brewed using hot freshly boiled water, by dissolving instant tea powders in water or in the form of ready-to drink teas in cans, bottles or cartons. Iced tea prepared from tea leaf with boiling water has the fresh brewed tea flavor/astringency enjoyed around the world. However, the steps of boiling water and cooling down can be time consuming, generally taking more than 30 minutes before the ice tea beverage is ready for consumption.

Convenient as cold water soluble tea powders can be, for many consumers the quality of the final beverage is not equal to that prepared from hot infused leaves. Many consumers prefer not to use instant tea powders as they perceive them to be lacking the fresh brewed tea taste and of inferior quality.

Accordingly, a leaf tea that can rapidly infuse in cold water to produce an iced tea beverage with the color and flavor of the traditionally hot brewed iced tea would offer the consumer a convenient option to both traditional leaf tea and powdered tea products. The benefit of a cold brew tea product is two folds, the convenience of not having to boil water and wait for it to cool down, and the fresh brewed tea taste.

There are numerous methods for making cold water soluble tea powders including U.S. Pat. No. 4,051,264 and U.S. Pat. No. 3,812,266. European patent specification EP 760,213 A1 (Unilever) discloses a method of enhancing color in a tea-based foodstuff. The method involves using a tannase pre-treatment (on leaf or extract) followed by treatment with exogenous peroxidase and hydrogen peroxide to generate cold-soluble color.

International patent publication WO 97/40699 (Unilever) concerns tea processing with zeolites to generate color. There are examples of adding zeolite following tannase treatment to generate cold-water soluble tea.

U.S. Pat. No. 4,639,375 discloses treating black tea with tannase, together with other cell-wall digesting enzymes, to generate cold-water soluble instant tea powders.

When conventional teas are extracted with cold water for short periods of time (less than 15 minutes), the tea beverage produced has a low concentration of extractable tea solids, a Very light color and almost no tea-like taste. Water at temperatures of about 100° C. is usually employed to obtain a satisfactory beverage with prior art tea leaves.

It has now been discovered that by appropriate selection of tea leaves, which are, in turn, subjected to appropriate processing, a cold brew tea beverage can be obtained. It is now possible to obtain a leaf tea that rapidly infuses and remains soluble in cold water to give a beverage with good color and flavor that is as acceptable to consumers as iced tea made from a hot infused black leaf tea. Furthermore, this product can be made from infusions of tea obtained by modifying the traditional black tea manufacturing process.

The inventive product is used to prepare a beverage with good color and taste by infusion in cold water. The product is comprised of 100% tea leaves and excludes the addition of instant tea powder or the coating of tea extracts onto the tea leaves. In other embodiments, the product may employ powders, extracts or colorants. The product infuses in cold water and can be used to produce an iced tea beverage with the color and flavor comparable to iced teas prepared by hot brewing methods.

In summary, this invention encompasses a tea leaf product that rapidly brews in cold water to produce a beverage with color and flavor characteristics substantially identical to hot brewed iced tea beverages and a process of manufacturing cold infusing black tea leaf. This product and processes for its preparation will be described in detail in the "Detailed Description of the Invention".

"Tea" for the purposes of the present invention means leaf material from *Camellia sinensis* var. *sinensis* or *Camellia sinensis* var. *assamica*. It also includes herbal teas such as rooibos tea obtained from Aspalathus linearis, however, most herbal teas are a poor source of endogenous fermenting enzymes. "Tea" is also intended to include the product of blending two or more of any of these teas.

"Leaf tea" for the purposes of this invention means a tea product that contains leaves of one or more tea origins in an uninfused form.

"Cold water infusible" for the purposes of this invention means giving good color, flavor and mouthfeel in a short infusion time, i.e., less that 10 minutes, but preferably within 5 minutes at a temperature at or below about 15° C.

As used herein, the word "comprising" is intended to mean including but not necessarily "consisting essentially of", "consisting of" or "composed of". In other words, "comprising" the listed steps or options need not be exhaustive.

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

DETAILED DESCRIPTION OF THE INVENTION

Evaluation of Cold Brew Product by Qualitative Descriptive Analysis (Q.D.A.)

The color and flavor, including mouthfeel, of iced tea beverages govern their acceptability. A Qualitative Descriptive Analysis (Q.D.A.) test method was selected to systematically characterize and quantify tea beverages based on color, flavor, and mouthfeel. The Q.D.A. method employs a trained panel of expert tasters to quantify the color, flavor and mouthfeel attributes of iced tea beverages relative to defined reference standards.

Expert tasters were chosen by screening prospective panel members for ability to taste standard solutions of acid (citric acid), salt (sodium chloride), sweet (sucrose), and bitter (caffeine) that represent high to low levels (grams per liter) of each flavor attribute as defined in the following table.

| Acid | Bitter | Salt | Sweet |
|------|--------|------|-------|
| 0.6  | 0.5    | 2.0  | 12.0  |
| 0.4  | 0.3    | 1.0  | 4.3   |
| 0.2  | 0.2    | 0.5  | 1.6   |
| 0.1  | 0.1    | 0.2  | 0.5   |

Individuals who were able to identify and differentiate the flavor of each test solution at the lowest concentration qualified for participation as an expert taster and were trained to describe and quantify tea beverages using a defined set of attributes to describe color, flavor and mouth feel.

Through a mathematical technique known as Principle Component Analysis four attributes, bitterness (also called bitterness2 or bitter 2 in this application which refers to the bitter aftertaste rather than initial bitterness), smoothness, redness and yellowness were found to be useful for differentiating iced tea beverages. Expert panelists (a minimum of eight) were selected and trained to describe iced tea beverages by rating the intensity of each key attribute (bitterness, smoothness, redness, and yellowness) on a scale of 1–10 by exposing the tasters to extremes of each attribute. For example an infusion of whole leaf Darjeeling tea may be used to define bitterness and yellowness and an infusion of Argentine tea may be used as an example of redness and smoothness. Once trained the expert tasters were tested through blind evaluations of iced tea beverages representing low to high levels of each attribute, provided in random order. Expert tasters evaluated each sample at least 3 times to be assured that panelist ratings were consistent and reproducible. To determine the range of attributes that defines hot brewed iced teas, a variety of teas that represent a broad sampling of the world of teas were evaluated by the trained panel after being prepared by three distinct methods of brewing. All of the water was carbon-filtered tap water. Brewing Method 1 (full flavored brew method) involved the preparation of a concentrate followed by dilution to final beverage strength. Six pitcher or family size tea bags each containing about 7.13 grams of tea leaf were brewed in two quarts of hot freshly boiled water for 30 minutes followed by dilution to beverage strength with an additional two quarts of cold water making a gallon of beverage. Brewing Method 2 (mild flavored brew method) was a single strength infusion rather than a concentrate preparation. In contrast to Method 1, the tea bags were brewed with the full amount of boiled water (four quarts) for three minutes. Brewing Method 3, designed for the cold brew tea leaf product, was used for the preparation of the inventive product and all reference teas. Six pitcher or family size tea bags were infused in one gallon of cold (60° F. or 15° C.) carbon filtered water by dunking the bags several times each minute during the 5 minute brewing time.

Product evaluations were conducted in Sensory booths where the trained expert tasters ranked the teas on a 1–10 scale for bitterness, smoothness, redness, and yellowness. The samples were served blind, identified only by a three-digit code and presented in three replications using a balanced block design. Flavor assessment was done under red lights. Appearance was done under white light. The result of this type of test over several different panels, while possibly not being an exact match as to absolute values, will still statistically show the same relative differences between the products.

The teas may be distinguished as those which when cold brewed are poor in color or flavor and are generally lacking in the desirable tea attributes as compared to the teas of the invention having good color and taste and generally attributes that are like those of hot brewed teas. The method for defining the teas is as follows: by plotting each color attribute (red or yellow) vs. a mouthfeel attribute (bitter or smooth), using averaged scores of the panelists, plots are produced which show the inventive teas as superior to other cold brewed teas.

The groupings that result indicate that the world of teas along with the described inventive tea fall in a region of the graphs that is distinct from simply cold brewing all other teas in the data set. The defining region of the group, or Q.D.A. map that relates to the invention, is shown in FIGS. 1, 2, 3 and 4 where teas lying in the region defined by equation 1, 2, 3 and 4, describe the area of applicants' invention. The teas lying outside of this defined region represent cold brewed teas selected from the world of teas that lack the preferred qualities by comparison. The type of tea, the method of brewing and the data points produced by the Q.D.A. analysis are reported in Table 1 below.

TABLE 1

Tea type; Brewing Method; Q.D.A. Score

| Samples | | Average of Q.D.A. Attributes | | | |
|---|---|---|---|---|---|
| ID | Description | Smooth | Bitter2 | Red | Yellow |
| #01 | Cold Brew Tea (Tannase Peroxide Process) 5 minute cold brew (Example 1) | 8.0 | 2.4 | 8.0 | 2.3 |
| #02 | Cold Brew Tea (Alkaline treatment process) 5 minute cold brew (Example 2) | 8.3 | 1.8 | 9.6 | 1.2 |
| #03 | Lipton ® Cup - 3 minute hot brew | 7.3 | 4.2 | 5.5 | 4.5 |
| #04 | Lipton ® Family - 3 minute hot brew | 7.2 | 3.6 | 5.8 | 4.3 |

TABLE 1-continued

Tea type; Brewing Method; Q.D.A. Score

| Samples | | Average of Q.D.A. Attributes | | | |
|---|---|---|---|---|---|
| ID | Description | Smooth | Bitter2 | Red | Yellow |
| #05 | Luzianne ® - 3 minute hot brew | 7.8 | 2.5 | 6.6 | 3.5 |
| #06 | Kenyan - 3 minute hot brew | 6.6 | 4.8 | 4.5 | 5.5 |
| #07 | Superdust - 3 minute hot brew | 6.9 | 3.9 | 8.5 | 1.9 |
| #08 | Ceylon - 3 minute hot brew | 6.3 | 5.3 | 3.6 | 6.4 |
| #09 | Assam - 3 minute hot brew | 6.4 | 4.4 | 5.2 | 4.9 |
| #10 | Darjeeling - 3 minute hot brew | 4.7 | 6.3 | 2.5 | 7.7 |
| #11 | Lipton ® Cup - 30 minute hot brew | 6.9 | 4.0 | 4.5 | 5.5 |
| #12 | Lipton ® Family - 30 minute hot brew | 7.3 | 3.4 | 6.5 | 3.6 |
| #13 | Luzianne ® - 30 minute hot brew | 7.8 | 2.7 | 6.0 | 4.1 |
| #14 | Kenyan - 30 minute hot brew | 6.4 | 4.3 | 6.1 | 4.0 |
| #15 | Superdust - 30 minute hot brew | 7.4 | 3.3 | 6.2 | 3.9 |
| #16 | Ceylon - 30 minute hot brew | 6.5 | 5.0 | 2.4 | 7.9 |
| #17 | Assam - 30 minute hot brew | 6.6 | 4.5 | 5.1 | 4.9 |
| #18 | Darjeeling - 30 minute hot brew | 5.2 | 6.4 | 1.8 | 8.8 |
| #19 | Lipton ® Cup - 5 minute cold brew | 9.0 | 1.5 | 1.3 | 9.4 |
| #20 | Lipton ® Family - 5 minute cold brew | 8.7 | 1.6 | 2.0 | 8.6 |
| #21 | Luzianne ® - 5 minute cold brew | 8.4 | 1.5 | 1.3 | 9.6 |
| #22 | Kenyan - 5 minute cold brew | 8.9 | 1.7 | 2.7 | 7.4 |
| #23 | Superdust - 5 minute cold brew | 8.5 | 1.7 | 1.6 | 8.8 |
| #24 | Ceylon - 5 minute cold brew | 8.1 | 2.5 | 2.6 | 8.0 |
| #25 | Assam - 5 minute cold brew | 8.8 | 1.5 | 1.6 | 9.3 |
| #26 | Darjeeling - 5 minute cold brew | 8.0 | 2.2 | 1.0 | 10.0 |

FIGS. 1 through 4 generally represent Q.D.A. maps comparing selected aspects of the tea as measured by the panelists.

BRIEF DESCRIPTION OF THE DRAWINGS

The figures of the instant application wherein Data from Table 1 is depicted graphically in FIGS. 1–4.

Figure 1:
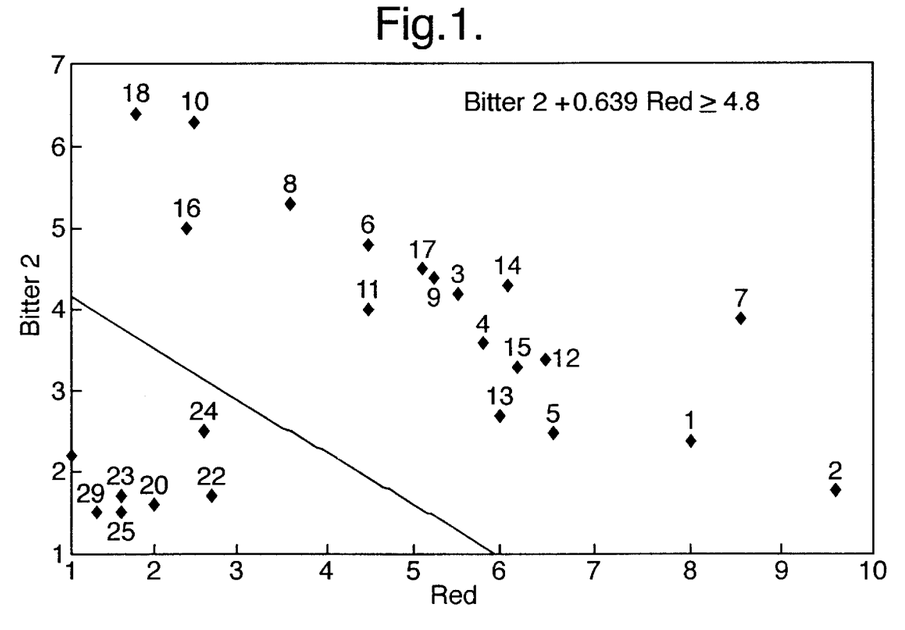
FIG. 1 is a plot of Red vs. Bitter2. The inventive area on the map is represented by the area on or above the line defined by the Equation Bitter $2+0.639$ Red $\geq 4.8$.

In FIG. 1 samples 1 and 2, the inventive products, fall in the area defined by high quality hot brewed teas with good color and taste. The commercial teas brewed cold fall in a separate area below the line.

Figure 2:
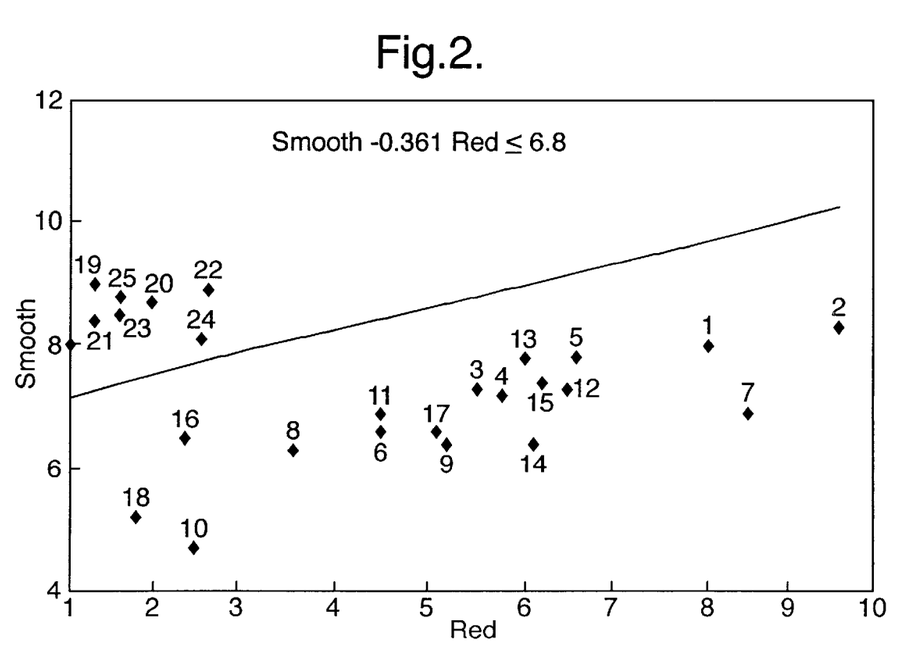
FIG. 2 is a plot of Red vs. Smooth. The inventive area on the map is represented by the area on or below the line defined by the Equation Smooth$-0.361$ Red $\leq 6.8$.

In FIG. 2 samples 1 and 2, the inventive products, fall in the area defined by high quality hot brewed tea with good color and taste. The commercial tea brewed cold falls in a separate non-preferred area above the line.

Figure 3:
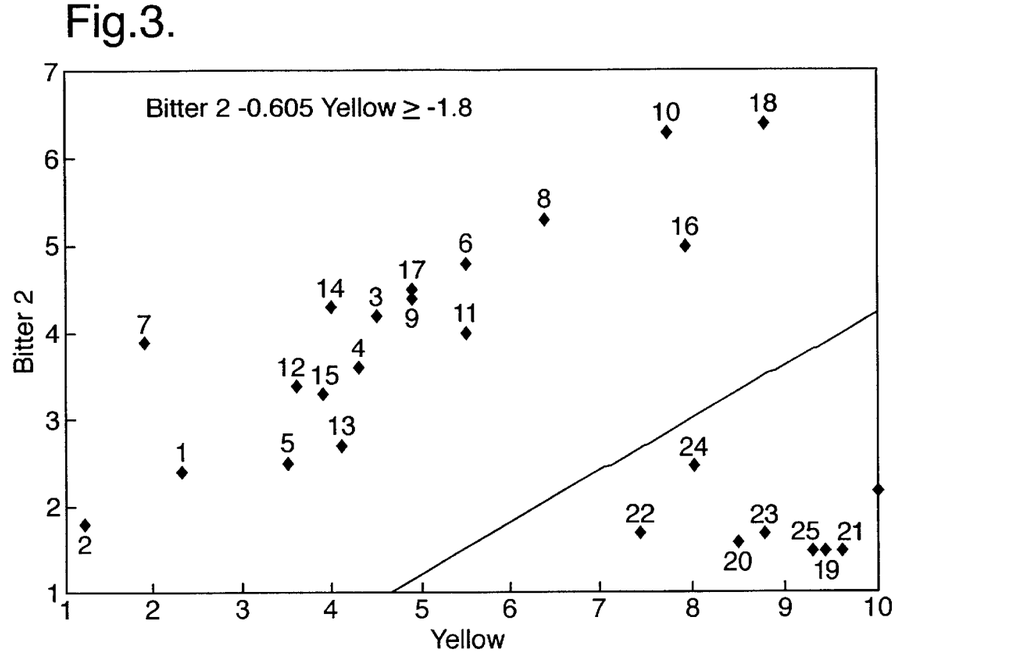
FIG. 3 is a plot of Yellow vs. Bitter2. The inventive area on the map is represented by the area on or above the line defined by the Equation Bitter $2-0.605$ Yellow $\geq -1.8$.

In FIG. 3 samples 1 and 2, the inventive products again fall with the high quality hot brewed teas. This graph is the mirror image of FIG. 1.

Figure 4:
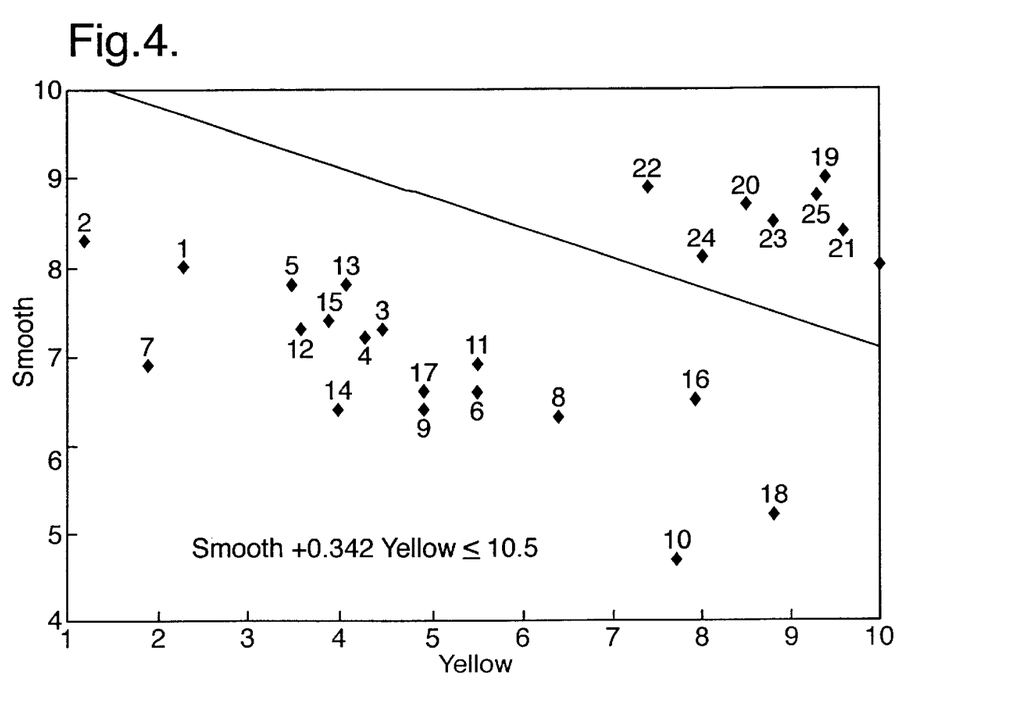
FIG. 4 is a plot of Yellow vs. Smooth. The inventive area on the map is represented by the area on or below the line defined by the Equation Smooth$+0.342$ Yellow $\leq 10.5$.

In FIG. 4 samples. 1 and 2, the inventive products fall with the high quality hot brewed teas. This graph is the mirror image of FIG. 2.

When the product is subjected to the Qualitative Descriptive Analysis test (Q.D.A. test), the inventive products will fall in certain areas of FIG. 1 as defined by the equation where the bitterness2 score plus 0.639 times the redness score is greater than or equal to 4.8 (Bitter$2+0.639$ red$\geq 4.8$). In FIG. 2, the inventive products fall in the area where the Smoothness score minus 0.361 times the redness score is less than or equal to 6.8 (Smooth$-0.361$ red$\leq 6.8$).

FIGS. 3 and 4 are similar.

Each time a QDA test is run the following teas are to be included as standard reference controls: Ceylon, Assam, Superdust, Kenyan, and Darjeeling brewed as described in the methods. The Q.D.A. attributes for these teas should match those in Table 1 plus or minus 10%. If these values are not within this range the results of the panel are to be considered invalid for defining the cold brew product.

Processes for Preparing Cold Water Infusible Leaf

There may be many methods of preparing tea leaves that infuse in cold water. This invention describes processes for preparing black tea leaf that unlike conventional black tea leaf, when infused in cold water, produces tea with color and taste superior than using conventional black leaf for cold infusion.

One method, which is preferred, is a tannase peroxide method described in a companion co-pending application T98-034(C).

Tannase/Peroxide Process

When conventional tea leaves are extracted with cold water for short periods of time (less than 15 minutes), the tea beverage produced has a low concentration of extractable tea solids, a very light color and almost no tea-like taste.

In a preferred embodiment of the method, freshly plucked green tea leaves are withered and macerated in the normal way using any of the techniques known to those skilled in the art of tea manufacturing.

In a first departure from traditional black tea manufacture, the macerated leaves are treated with tannase (flavanol gallate esterase) to generate degailated catechins and gallic acid. This subsequently leads to the generation of theaflavins, epitheaflavic acids and non-gallated thearubigens during fermentation (which are more cold water soluble than the gallated ones).

The general reaction catalyzed by tannase is the cleavage of gallate ester linkages, both on gallated catechins and also from other gallated compounds within the leaf. Tannase is also well known to improve the clarity of tea products since galloyl groups are important in tea cream formation and tannase has been used extensively for the degallation and solubilization of black tea cream. The tea is fermented under solid state conditions.

The tannase can be applied using a variety of known techniques. It is preferred to dissolve tannase in water, spray the solution onto the macerated tea or dhool and leave the mixture to react for a suitable time at suitable fermentation temperatures. The tannase is applied to the dhool after an initial maceration (for example, a first CTC cut) in a fine spray followed by subsequent cutting (for example, a second or third CTC cut) to ensure adequate mixing. The dhool is preferably incubated under vacuum or under anaerobic conditions for example in an atmosphere of nitrogen to prevent fermentation. It is preferable that complete degallation takes place before fermentation starts as this results in maximal formation of gallate ester free theaflavin, epitheaflavic acids and thearubigens during the subsequent fermentation, which in turn leads to optimal cold soluble color generation.

A method has been developed for bringing certain exogenous compounds into contact with endogenous compounds found in tea. This involves vacuum infiltrating macerated tea leaves with those exogenous compounds to modify certain properties of tea and tea based beverages. For example, an infusion of tannase pre-treated tea has been found to have more than double the total theaflavin content of a control and a sixfold increase in theaflavin 1 monogallate 1.

Vacuum infiltration is a technique that is often used in the preparation of protoplasts from plant tissue, albeit to introduce substances between rather than into cell walls. Cut tea leaf tissue is incubated in a solution containing tannase. The suspension is then placed under vacuum and air is drawn from the intracellular spaces of the leaf particles, the enzyme solution is drawn in to replace it. It has been found that a vacuum of less than 100 mbar is suitable for this.

The major constraint when applying this method to tea dhool is achieving access within the cells. Another major problem is that large volumes of water can seriously affect the quality of the tea by reducing oxygen uptake during fermentation. Vacuum infiltration is a useful tool for introducing enzymes, for example tannase, into solid state dhool. When fermented, tannase treated dhool gives rise to black tea with high levels of theaflavin and no gallated species. This enables one to produce a range of novel teas. Vacuum assisted tannase treatment is much more effective in removing gallated species and enhancing additional theaflavin formation than the equivalent treatment under ambient temperature and pressure. The vacuum allows the enzyme to penetrate the tissue and remove gallated species prior to fermentation, the key feature of tannase driven theaflavin enhancement, compared to simply applying the enzyme onto fermenting dhool and mixing in by hand.

If at all possible the conditions should be adjusted to prevent any fermentation prior to or during tannase treatment. This can be achieved by using a stronger vacuum pump, holding the dhool under $N_2$ sparge or shortening the tannase treatment.

Tannase can be applied to the macerated tea by a simple dosing. However, spraying the tannase in a fine mist is preferable as it aids infiltration.

Suitable conditions can be readily determined by experiment. Good results have been obtained with tannase in an amount of 10 mg/kg dhool but preferably between 40 and 80 mg/kg dhool. The activity of tannase is 50,000 units per gram.

Fermentation is preferably carried out at a pH in the range of 4.0 to 6.5. The fermentation temperature is preferably in the range 15 to 40° C. Fermentation is preferably carried out for a time in the range 30 to 150 minutes, more preferably 105 to 120 minutes.

Furthermore, in a second departure from traditional black tea manufacture hydrogen peroxide is added, after a time that is sufficient to generate gallic acid and theaflavin during the fermentation step, to activate (or at least greatly enhance the activity of) endogenous tea leaf peroxidase.

Tea is known to contain natural peroxidase at high levels. It is also known that natural peroxidase can be activated (or have its activity enhanced) through the addition of hydrogen peroxide in a slurry system. J. Sc. Food Agric. vol. 32, p 920-032 (Dix., 1981) discloses such a system and process. The article mentions that peroxidase can oxidize tea polyphenols to form theaflavins, and also thearubigens that may be similar and different to those produced under "normal" fermentations. However, it does not offer any detailed understanding as to the chemistry at work.

It has been found that the endogenous peroxidases have the potential to oxidize catechins to theaflavins and thearubigens, convert theaflavins to thearubigens and, unlike endogenous polyphonol oxidase, readily oxidize gallic acid to form epitheaflavic acids. The combination of these reactions generates significant amounts of colored compounds that are soluble in cold water.

The hydrogen peroxide is added in an amount that is sufficient to activate endogenous peroxidases and oxidize gallic acid liberated by the tannase treatment. One skilled in the art can determine that by experiment. It is preferred to use between 100 and 200 ml of 2.0 to 2.5% hydrogen peroxide per kg dhool, but preferably 160 ml of 2.0% hydrogen peroxide per kg dhool. Under normal conditions of tea manufacture, peroxidase is largely inactive, due to the low endogenous levels of hydrogen peroxide and high activities of catalase. Measurements have shown that all added hydrogen peroxide is consumed during the process, with none remaining in the final made tea. In contrast to the findings disclosed in the aforementioned U.S. Pat. No. 4,051,264, it has been found that the combination of tannase treatment and subsequent activation of peroxide is critical for the manufacture of a product that gives good color and acceptable taste. Product that was only tannase treated had a "sour" or "metallic" note and dose not produce a tea beverage with acceptable color when brewed in cold water.

The method of the invention will now be described with reference to Example 1.

EXAMPLE 1

Lab scale process

Process steps—60 mg tannase dissolved in 24 ml water was sprayed onto 100 g of frozen dhool. The dhool was then thawed under $N_2$ and once it had reached 20° C., it was placed under vacuum (50 mbar) for 60 minutes. The dhool was then fermented for 60 minutes at 25° C., 100% RH. After fermentation the dhool was sprayed with 12.5 ml~2% hydrogen peroxide solution, placed under vacuum for 15 minutes and then dried by a fluid bed drier. One can increase the level of theaflavins by pre-treating the dhool with tannase. Peroxide is added to activate the endogenous tea peroxidase. This enzyme oxidizes theaflavins and the gallic acid released by tannase to give dark, cold water soluble pigments.

Alkaline Treatment Process

In another embodiment of the invention a cold soluble tea ingredient t is prepared by selective alkaline treatment of black tea leaves. The alkaline treated black tea leaf rapidly infuses in cold water providing color to iced tea beverages and when appropriately mixed in selected amounts with other black teas results in a cold infusible beverage with the full complement of tea flavor and color associated with the corresponding prior art processes. It is important that the particle size of the tea ingredient and the resulting leaf tea product be of a suitable size to allow rapid and full infusion in cold water. This alkaline treated product in selected amounts about 5% to 25% then may be added to highly flavored tea about 75% to 95% to produce a cold water infusible tea leaf product with both good color and good taste.

As mentioned above, the alkaline treatment step includes conversion of tea compounds to highly colored species.

In this embodiment, it is found that tea leaf products which are capable of producing a high quality tea beverage upon brewing with either cold or hot water and which have a substantially reduced level of cold water insoluble solids are obtained by contacting black tea leaf with alkali, thereafter, neutralizing the alkali with acidic reagents, drying the leaf and combining it with selected highly flavored teas.

The resulting leaf tea blends produce beverages prepared from cold water which have a full measure of the organoleptic properties of prior art tea leaf products brewed with hot water. The products of the invention have the unique property of producing high quality tea beverages when brewed with cold water, whereas prior art conventional tea leaf products are only poorly extracted by cold water. For this reason, prior art tea leaf products require boiling water to prepare a full-flavored beverage.

Figure 5:
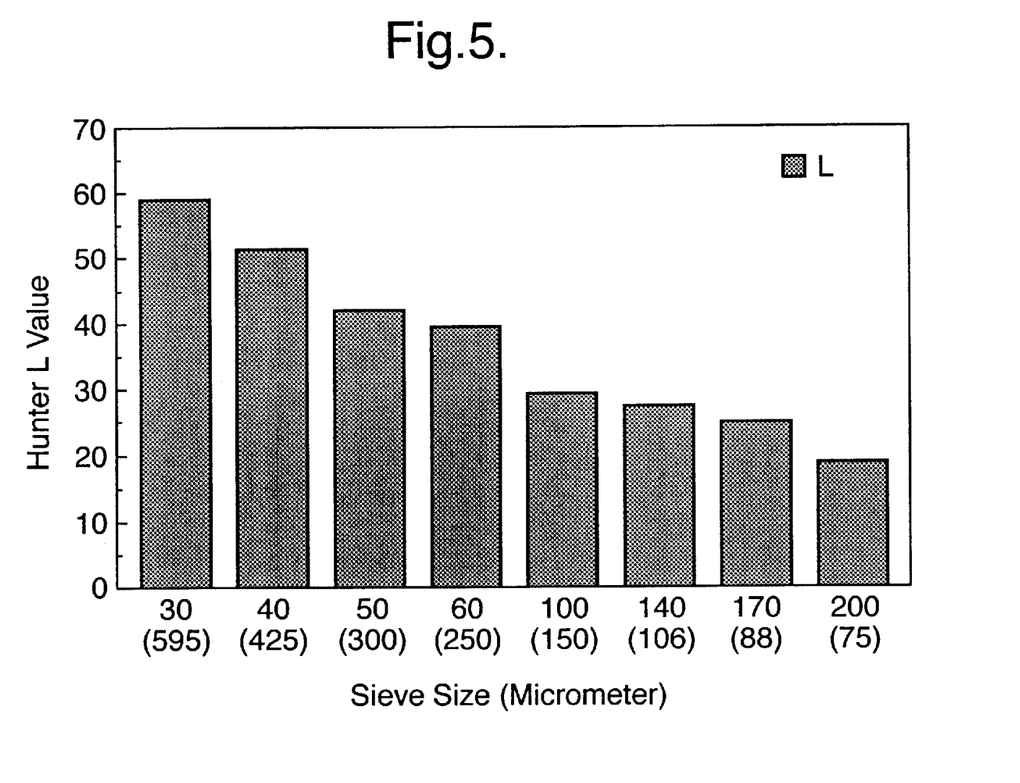
FIG. 5 shows the relationship of flavor and color of the tea with changes in the particular size.

Particle size control is necessary for non alkaline treated leaves and desirable for alkaline tea to break up agglomerated particles treated; a minimum size is required so it does not dust through tea bags and produce haze. Flavor and color of the tea are improved with decreasing particle size as shown in FIG. 5.

This second embodiment of the invention will now be described in Example 2.

EXAMPLE 2

In this Example, color was measured using the Hunter Lab DP 9000 with a sample path length of 5 cm. The color was analyzed by means of the L value. Control values refer to the color before treatment.

The Alkaline Treatment Process and a test procedure to evaluate the final product is given below.

| Materials: | Quantity: |
|---|---|
| Tea leaf | 20 lbs. |
| 45% KOH | 12 lbs. |
| Water | 9 lbs. |
| 95.7% Sulfuric Acid | 3.7 lbs. |
| Water | 9.0 lbs. |

Procedure:

The KOH and water were mixed and the diluted caustic solution was added to the 20 lbs. of tea leaf. The slurry was mixed well. The temperature of the leaf was raised to 77° C. and the slurry was aerated and mixed well for five minutes. 3.7 lbs. of sulfuric acid was mixed with 9 lbs. of water and added to the alkaline oxidized leaf to neutralize it. The neutralized leaf was dried to about 3 to 7% moisture at about 70° C.

Product Evaluation 2.27 grams of dry Alkaline Treated Leaf was added to a 300 ml beaker and 200 ml of 15° C. tap water was added to the beaker. The slurry was stirred several times every minute for five minutes and the leaf was separated from the extract by filtration through tea paper. A one-quarter dilution of the extract was prepared by mixing 50 ml of the extract with 150 ml of tap water. The diluted extract was then evaluated with a Hunter Colorimeter.

A Hunter L value of about 15–25 and a Hunter "a" value of 20–25 should be obtained for this sample.

EXAMPLE 3

A series of tests were run to evaluate the cold infusion Hunter L value of a broad sampling of teas. The alkaline treated tea of the invention was compared for color and produced an overwhelmingly better color.

The teas were brewed and their Hunter L values are presented in Table 2 below.

TABLE 2

| Sensory Code | Sample | Hunter L Value |
|---|---|---|
| 124 | Tetley ® North | 51.2 |
| 136 | Luzianne ® Cup | 71.6 |
| 251 | Lipton ® Cup | 62.1 |
| 583 | Salada ® | 61.1 |
| 685 | Red Rose ® Cup | 60.1 |
| 692 | Tetley ® South | 71.1 |
| 856 | Lipton ® Family | 65.4 |
| 000 | Alkaline treated tea* | 23.2 |

*This sample contained 17.5% Alkaline Treated tea and 82.5% non-treated highly flavored teas.

The "cold infusion" Hunter L Value is a measurement of color obtained by adding 2.27 gram of tea leaves in a bag to 200 ml of carbon filtered tap water at 15° C. and infusing the bag for five minutes with occasional stirring. Separating the bag from the liquid extract, adjusting the pH to 5.0 with dilute $H_2SO_4$, diluting 50 ml of the extract to 200 ml with deionized water and measuring in a Hunter DP 9000 Colorimeter. Other parameters were described earlier in the Q.D.A. analysis above where the alkaline treated tea is designated number 2 from Table 1.

The tea of Example 3 was placed in a bag and used to prepare fresh brewed iced tea using a cold water infusible black tea leaf bag that delivers the equivalent flavor and color of hot-brewed iced tea. The cold water infusible tea bag contains 82.5% highly flavored teas having smaller particle sizes so that they infuse more easily and quickly in cold water and 17.5% alkaline oxidized tea to boost the color.

A preference test was conducted comparing iced tea made using the cold water infusible tea bag (brewed for 5 minutes using 60° F. water and cooled to 40° F.) to iced tea made from commercial Lipton® family size tea bags (hot brewed for 3 minutes and cooled to 40° F.). The respondents were given the option of putting the additives they normally put into fresh brewed tea (lemon, sugar, and aspartame). No significant differences in "liking scores" were detected between the cold water infusible tea and the hot brewed Lipton iced tea. Both samples were rated slightly above "like slightly" and 31 respondents preferred the hot brewed iced tea compared to 18 preferring the cold brewed iced tea.

SAMPLE INFORMATION

| Sample | Variable |
|---|---|
| Control | Iced tea made with Lipton ® Family Size tea bag 3 minute hot brew |
| Test | Iced tea made with Cold Water infusible tea bag 5 minute cold brew |

SENSORY METHOD

Samples were evaluated in a preference test by 49 in-house employee users/acceptors of iced tea made from tea bags. Samples were served in clear plastic cups and presented in the booths under white lights, using balanced presentation orders. Respondents were given the option of adding lemon, sugar, or aspartame to the tea.

TABLE 3

ICED TEA MADE FROM TEA BAGS
COLD BREW BLEND VS. HOT BREW TEA
FROM LIPTON ® FAMILY OR PITCHER BAG
Acceptability/Preference Test Results*
(n = 49)

| | Sample | Mean Rating | # Preferring |
|---|---|---|---|
| Control | Hot Brew Lipton Bags | 6.5 | 31 |
| Test | Cold Brew Tea Bags | 6.1 | 18 |

*No significant differences between the samples for acceptability or preference at the 95% level of confidence.
Scale:
9 = Like extremely
8 = Like very much
7 = Like moderately
6 = Like slightly
5 = Neither like or dislike
4 = Dislike slightly
3 = Dislike moderately
2 = Dislike very much
1 = Dislike extremely Based on the acceptability scores, it can be concluded that there are no significant differences between iced tea prepared using Cold Brew tea bags and hot-brewed Lipton iced tea in "liking scores".

Instant Tea Coating Method

A third and less preferred method of preparing cold infusion tea is to treat standard tea leaves with instant tea powder or to coat the tea leaves with tea extracts. Instant tea powders or solutions may also be employed alone or in combination with other colorants but these products would not be considered 100% leaf tea formulations. Depending on the manufacture of the powder or tea concentrate, low amounts as well as high amounts of these tea ingredients may be added in sufficient quantities to provide color of a typical hot brew tea product. Products made by this method are expected to have a less preferred flavor.

This is illustrated in Example 4 below:

EXAMPLE 4

| Weight. Instant Powder added to bag | Control | Commercial Instant 1 | | | Commercial Instant 2 | | |
|---|---|---|---|---|---|---|---|
| | 0.00 | 0.1 gm | 0.15 gm | 0.2 gm | 0.1 gm | 0.15 gm | 0.2 gm |
| Hunter L value | 49.6 | 34.9 | 23.9 | 20.1 | 35.7 | 33.0 | 32.4 |
| Hunter a value | 16.2 | 28.9 | 29.0 | 27.3 | 22.9 | 22.5 | 30.3 |
| Hunter haze | 10.4 | 14.7 | 19.3 | 22.2 | 26.9 | 34.2 | 40.5 |

All samples are brewed in tea bags using 2.27 grams of tea per bag. Bags are brewed at 15° C. for 5 min. in tap water of 170–180 ppm hardness using a LA Motte test kit.

As is clear from the foregoing, various modifications of the present invention may be made without departure from the spirit and scope of the disclosure, and the invention may be practiced suitably in the absence of elements not specifically disclosed herein.

What is claimed is:

1. A cold brew tea beverage prepared by a cold brew method said beverage having taste and color parameters so that
   i. when a Q.D.A. test is performed evaluating Bitter2 and Red, and
   ii. when Bitter2 is plotted on a Q.D.A. map as the Y axis and red is plotted on said map as the X axis
   the beverage has a Q.D.A. score on or above the line defined by: Bitter 2+0.639 Red≧4.8
   wherein the beverage is prepared from cold water infusable tea leaves having been fermented in the presence of tannase and subjected to hydrogen peroxide after the generation of gallic acid and theaflavin, and in an infusion time of less than 30 minutes and at a temperature at or below about 20° C.

2. A black tea product in either loose or bag form comprising tea leaves which is used to prepare a cold beverage having taste and color parameters so that
   i. when a Q.D.A. test is performed evaluating Bitter2 and Red, and
   ii. when Bitter2 is plotted on a Q.D.A. map as the Y axis and red is plotted on said map as the X axis
   the beverage has a Q.D.A. score on or above the line defined by: Bitter 2+0.639 Red≧4.8
   wherein the black tea product is prepared from cold water infusable tea leaves having been fermented in the presence of tannase and subjected to hydrogen peroxide after the generation of gallic acid and theaflavin, and in an infusion time of less than 30 minutes or less and at a temperature below about 20° C. or less.

3. The product according to claim 2 prepared from tea leaves obtained by macerating green tea leaves, treating the macerated leaves with tannase, fermenting the tannase-treated macerate for a time that is sufficient to generate gallic acid and theaflavin, continuing the fermentation in the presence of an amount of hydrogen peroxide that is sufficient to activate endogenous peroxidases, and drying resulting fermented leaf material to yield the cold water infusing leaf.

4. A cold water infusing leaf tea product obtainable by macerating green tea leaves, treating the macerated leaves with tannase, fermenting the tannase-treated macerate for a time that is sufficient to generate gallic acid and theaflavin, continuing the fermentation in the presence of an amount of hydrogen peroxide that is sufficient to activate endogenous peroxidases, and drying the fermented leaf material to yield the cold water infusing leaf tea as defined in claim 1.

5. The product as defined in claim 4 wherein a vacuum is employed to assist in treating the macerated leaves with tannase.

6. The product as defined in claim 4 wherein the tannase treatment is carried out under anaerobic conditions.

7. The product according to claim 3 wherein between 40 mg and 80 mg of tannase is used per kg of dhool.

* * * * *